(12) United States Patent
Wershofen et al.

(10) Patent No.: US 11,406,964 B2
(45) Date of Patent: Aug. 9, 2022

(54) HETEROGENEOUS CATALYSTS FOR THE SYNTHESIS OF CARBAMATES

(71) Applicant: Covestro Intellectual Property GmbH & Co. KG, Leverkusen (DE)

(72) Inventors: Stefan Wershofen, Mönchengladbach (DE); Anton Vidal-Ferran, Cologne (DE); José Luis Núñez Rico, Motbrio del Camp (ES); Javier Perez-Ramirez, Zürich (CH); Begona Puertolas Lacambra, Zürich (CH); Amol P. Amrute, Lund (SE)

(73) Assignee: Covestro Intellectual Property GmbH & Co. KG, Leverkusen (DE)

( * ) Notice: Subject to any disclaimer, the term of this patent is extended or adjusted under 35 U.S.C. 154(b) by 93 days.

(21) Appl. No.: 17/040,572

(22) PCT Filed: Mar. 26, 2019

(86) PCT No.: PCT/EP2019/057541
§ 371 (c)(1),
(2) Date: Sep. 23, 2020

(87) PCT Pub. No.: WO2019/185608
PCT Pub. Date: Oct. 3, 2019

(65) Prior Publication Data
US 2021/0053031 A1    Feb. 25, 2021

(30) Foreign Application Priority Data

Mar. 28, 2018 (EP) .................................... 18164463
Jan. 15, 2019 (EP) .................................... 19151926

(51) Int. Cl.
| B01J 23/10 | (2006.01) |
| B01J 6/00 | (2006.01) |
| B01J 37/03 | (2006.01) |
| B01J 37/12 | (2006.01) |
| C07C 269/04 | (2006.01) |
| C07C 271/28 | (2006.01) |

(52) U.S. Cl.
CPC ............... *B01J 23/10* (2013.01); *B01J 6/001* (2013.01); *B01J 37/031* (2013.01); *B01J 37/12* (2013.01); *C07C 269/04* (2013.01); *C07C 271/28* (2013.01)

(58) Field of Classification Search
CPC . B01J 23/002; B01J 23/10; B01J 6/001; B01J 37/031; B01J 37/12; C07C 269/04; C07C 271/28
See application file for complete search history.

(56) References Cited

U.S. PATENT DOCUMENTS

| 4,268,684 A | 5/1981 | Gurgiolo |
| 6,133,194 A * | 10/2000 | Cuif ..................... C01G 25/02 |
| | | 502/170 |
| 10,336,681 B2 | 7/2019 | Ranade et al. |
| 10,703,714 B2 | 7/2020 | Kelkar et al. |
| 2008/0227999 A1 | 9/2008 | Molzahn |
| 2011/0124902 A1 | 5/2011 | Corma Canos et al. |
| 2011/0237823 A1 | 9/2011 | Tundo et al. |
| 2012/0264587 A1 | 10/2012 | Schermanz et al. |
| 2013/0244867 A1 | 9/2013 | Wershofen et al. |

FOREIGN PATENT DOCUMENTS

| CN | 1626437 A | 6/2005 |
| CN | 103694141 A | 4/2014 |
| CN | 107715857 A | 2/2018 |
| WO | WO 9947493 A1 | 9/1999 |

OTHER PUBLICATIONS

International Search Report, PCT/EP2019/057541, dated Jun. 26, 2019, Authorized officer: Oliver Beckmann.
Zhang et al., Ind. Eng. Chem. Res. 2002, 41, 5139-5144.
Li et al., Chin. J. Catal. 2003, 24, 639-642.
Wang et al., Ind. Eng. Chem. Res. 2006, 45, 4892-4897.
Wang et al., J. Chem. Technol. Biotechnol. 2009, 84, 48-53.
Corma et al., Angew. Chem. Int. Ed. 2010, 49, 1286-1290.
Tomishige et al., Green Chem., 2011, 13, 3406-3413.
Corma et al., Angew. Chem. Int. Ed. 2012, 51, 4190-4193.
Corma et al., Pure Appl. Chem. 2012, 84, 685-694.
J. Appl. Cryst. 11 (1978), 102-113.
J. Am. Chem. Soc. 1938, 60, 309.
Pappacena et al., Int. J. Hydrogen Energy 2012, 37, 1698-1709.
Stud. Surf. Sci. Catal. 2010, 175, 835-838.
Raquel Juarez et al: "Activity of ceria and ceria-supported gold nanoparticles for the carbamoylation of aliphatic amines by dimethyl carbonate", Pure & Applied Chemistry, vol. 84, No. 3, Sep. 19, 2011, pp. 685-694, XP055504079.

* cited by examiner

*Primary Examiner* — Brian A McCaig
(74) *Attorney, Agent, or Firm* — Donald R. Palladino

(57) ABSTRACT

The present invention relates to a catalyst for preparing carbamates, in particular aromatic carbamates, comprising a binary oxide having the formula $L_{1-x}M_xO_2$, wherein L is a metal selected from the lanthanoid series and M is a metal selected from the group consisting of Sc, Y, Ti, Zr, Hf, metals from the lanthanoid series and metals from the actinoid series, and wherein x ranges from 0.01 to 0.05. The present invention also relates to a method for producing said catalysts and a method of utilizing said catalysts in the production of carbamates, in particular aromatic carbamates.

16 Claims, No Drawings

HETEROGENEOUS CATALYSTS FOR THE SYNTHESIS OF CARBAMATES

CROSS-REFERENCE TO RELATED APPLICATION

This application is a national stage application under 35 U.S.C. § 371 of PCT/EP2019/057541, filed Mar. 26, 2019, which claims the benefit of European Application No. 18164463.4, filed Mar. 28, 2018 and European Application No. 19151926.3, filed Jan. 15, 2019, each of which is incorporated herein by reference.

FIELD

The present invention relates to a catalyst for preparing carbamates, in particular aromatic carbamates, comprising a binary oxide having the formula $L_{1-x}M_xO_2$, wherein L is a metal selected from the lanthanoid series and M is a metal selected from the group consisting of Sc, Y, Ti, Zr, Hf, metals from the lanthanoid series and metals from the actinoid series, and wherein x ranges from 0.01 to 0.05. The present invention also relates to a method for producing said catalysts and a method of utilizing said catalysts in the production of carbamates, in particular aromatic carbamates.

BACKGROUND

Carbamates are valuable intermediates in the production of agrochemicals, dyes, pharmaceutical compounds and, in particular, aromatic isocyanates used in the synthesis of polyurethanes. Most relevant from a commercial point of view are carbamates derived from 4,4'-methylenediphenylamine (MDA), its isomers and/or homologues or mixtures of the aforementioned compounds as obtained by acid-catalysed condensation/rearrangement reaction of aniline and formaldehyde, as well as 2,4-toluenediamine (TDA) or technical mixtures of the two TDA isomers 2,4-TDA and 2,6-TDA (approximately 80/20 mixtures). The aforementioned aromatic amines are used in the preparation of methylene diphenyl diisocyanate (MDI) and toluene diisocyanate (TDI), which are the direct precursors of polyurethanes. At present, these isocyanates are produced industrially by phosgenation of the corresponding amines, a process which employs a toxic reagent (phosgene) and leads to large amounts of hydrogen chloride as side-product.

In the prior art, processes are known for the production of carbamates based on the functionalization of aromatic amines $Ar—NH_2$ with organic carbonates $ROCO_2R$ in the presence of suitable catalysts, according to the following scheme:

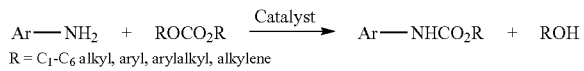

$R = C_1-C_6$ alkyl, aryl, arylalkyl, alkylene

In the case of aromatic diamines $Ar(—NH_2)_2$, biscarbamates are formed in a two-step reaction, with the corresponding monocarbamates being formed as intermediates, according to the following scheme:

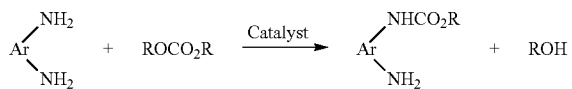

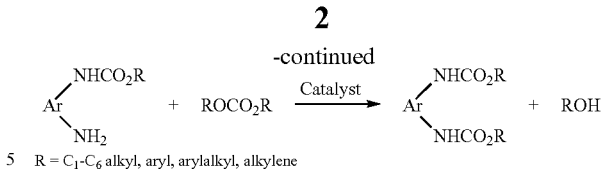

$R = C_1-C_6$ alkyl, aryl, arylalkyl, alkylene

Taking into account the alkylating properties of organic carbonates, N-alkylation competes with N-alkoxycarbonylation, and consequently N-alkylated amines, and N-alkylated carbamates might be formed along the reaction, in addition to the target carbamates.

Homogeneous as well as heterogeneous catalysts have been reported for carbamate formation.

Homogeneous catalysis suffers from difficult recovery of the catalyst from the reaction mixture, highly energy-intensive purification methods of the reaction products, impractical re-usability of the catalyst and in consequence possible generation of toxic and/or harmful wastes depending on the selected catalyst.

Heterogeneous catalysis, in principle, offers the possibility of overcoming many of these drawbacks: Catalysts can be easily recovered which simplifies re-use tremendously (although deactivation during the reaction time and/or upon cycling may put limits to recyclability). Although some of the catalysts reported in the prior art are toxic, this toxicity poses far less problems than in the case of homogeneous catalysis since the catalyst can be easily separated from the final product. In addition, since re-using the catalyst is generally possible at least for a limited number of cycles, the production of toxic waste is in any case reduced as compared to homogeneous catalysis. However, heterogeneous catalysis for alkoxycarbonylations may, just as homogeneous catalysts, suffer from the formation of undesired N-alkylated by-products.

The present invention deals with heterogeneous catalysis for carbamate production. Heterogeneous catalysis for carbamate production has been known in the art for some time: U.S. Pat. No. 4,268,684 describes a process for preparing carbamates in the presence of a catalyst which comprises at least one member selected from the group consisting of (1) tetravalent alkyl tin compounds or tetravalent alkyl tin oxides; and (2) zinc oxide.

WO 1999/047493 A1 describes a method for the preparation of organic carbamates in the presence of a heterogeneous metal based catalyst wherein the catalyst comprises a metal selected from the group consisting of Ti, Zr, Mn, Fe, Co, Ni, Cu, Zn, Sn, Pb, Bi and Cd.

WO 2007/015852 describes a process for the preparation of aromatic carbamates comprising contacting one or more organic carbonates with an aromatic amine or urea in the presence of a catalyst and recovering the resulting aromatic carbamate product, characterized in that the catalyst is a heterogeneous catalyst comprising a group 12-15 metal compound supported on a substrate.

US 2011/0237823 A1 describes a continuous process for the production of an aromatic urethane from the reaction of an aromatic amine and an organic carbonate in a fixed-bed reactor comprising at least alumina, silica, silica-alumina, activated carbon, titania, zirconia or diatomaceous earth.

US 2011/0124902 A1 describes a method for preparing a carbamate which comprises the reaction between at least an amine or a polyamine, an organic carbonate (OR)(OR')C=O and a catalyst which is formed by at least a support selected from at least a metal oxide, a microporous material, a mesoporous material, an anionic laminar compound and an organic polymer. If the catalyst is a metal oxide, it is selected from at least one of the following oxides: $Al_2O_3$, MgO, CaO, $Cu_xO_y$, $CO_xO_y$, $Fe_xO_y$, $Ce_xO_y$, $Cr_xO_y$, $ZrO_2$, and $Y_2O_3$.

US 2013/0244867 A1 discloses a heteropolyacid as the active component of the catalyst. The catalyst support comprises a metal oxide or a metalloid oxide consisting of zirconium oxide, titanium oxide, zinc oxide, silicon oxide, magnesium oxide, calcium oxide, tin oxide, barium oxide, cerium oxide, lanthanum oxide, vanadium pentoxide, aluminum oxide and mixtures thereof.

Zhang et al., *Ind. Eng. Chem. Res.* 2002, 41, 5139-5144 disclose an activated carbon-supported $ZnCl_2$ catalyst for the synthesis of methylene diphenyl-4,4'-diisocyanate from the reaction of aniline and dimethyl carbonate.

Li et al., *Chin. J. Catal.* 2003, 24, 639-642 disclose $In_2O_3/SiO_2$ for the synthesis of methyl N-phenyl carbamate by methoxycarbonylation of aniline with dimethyl carbonate.

Wang et al., *Ind. Eng. Chem. Res.* 2006, 45, 4892-4897 disclose $ZrO_2/SiO_2$ for the synthesis of methyl N-phenyl carbamate from aniline and dimethyl carbonate.

Wang et al., *J. Chem. Technol. Biotechnol.* 2009, 84, 48-53 disclose $ZnO-TiO_2$ for the preparation of methylene diphenyl diisocyanate via the synthesis of methyl N-phenyl carbamate by the reaction of aniline and dimethyl carbonate.

Corma et al., *Angew. Chem. Int. Ed.* 2010, 49, 1286-1290 disclose gold on ceria for the dialkoxycarbonylation of 2,4-diaminotoluene with dimethyl carbonate.

Tomishige et al., *Green Chem.*, 2011, 13, 3406-3413 disclose $CeO_2$ for the one-pot synthesis of methyl benzylcarbamate from benzylamine, $CO_2$ and methanol.

Corma et al., *Angew. Chem. Int. Ed.* 2012, 51, 4190-4193 disclose $CeO_2$ nano-octahedra preferentially exposing {111} facets as being highly active and selective for the dialkoxycarbonylation of 2,4-diaminotoluene with dimethyl carbonate in comparison to nanorods and nanocubes.

Corma et al., *Pure Appl. Chem.* 2012, 84, 685-694 disclose nanoparticulated $CeO_2$ being applied in the reaction of aliphatic amines with dimethyl carbonate to increase the conversion and selectivity towards alkoxycarbonylation vis-à-vis N-methylation. This increase in catalytic activity and selectivity towards alkoxycarbonylation is even increased by deposition of Au nanoparticles on $CeO_2$.

The international patent application WO 2016/151602 A2 relates to a process for the synthesis of dialkyl carbonates catalysed by a catalyst composition defined as "AB oxides", wherein A and B are rare earth metals or A and B are combinations of rare earth and transition metals with ratios ranging from 0.5:10 to 10:0.5. This definition covers a huge range of possible metal combinations including metals that can occur in more than one oxidation state, whereby the number of possible compounds falling under said definition is increased even further. The application discloses the compound "CeZrO", which, however, cannot be considered a chemical formula since this would require cerium and zirconium both having the oxidation state +1 which is unreasonable. The only specific disclosure of compounds falling under the definition of "AB oxides" is given in the examples. More particularly, a molar ratio of Ce to Zr of 3:1 is disclosed in Example 1. Assuming an oxidation state of +4 for either metal in the final catalyst (which is not sure beyond doubt since the starting material cerium nitrate does occur in two oxidations states and it is not specified which was used; also, it is not specified whether the final calcination step is carried out in the presence or absence of oxygen), this corresponds to the formula $Ce_{0.75}Zr_{0.25}O_2$. Example 6 discloses compounds of formula $Ce_{(1-x)}M_xO_2$, wherein only M=Zr is specifically mentioned. Ratios Ce:Zr of 1:1, 2:1, 3:1 and 5:1 are disclosed, corresponding to formulas $Ce_{0.5}Zr_{0.5}O_2$, $Ce_{0.666}Zr_{0.333}O_2$, $Ce_{0.75}Zr_{0.25}O_2$ and $Ce_{0.835}Zr_{0.165}O_2$. Compounds with a very low value of x, such as 0.05, 0.045, 0.02 or even 0.01, are not disclosed. Chinese patent application CN 103 694 141 A relates to a method of synthesizing phenylcarbamate. The catalyst used is a single metal oxide or a composition of two metal oxides, or comprises a catalytic active component and a catalyst carrier. An example of a catalyst that is specifically disclosed is a catalyst containing 50 wt.-% $CeO_2$ and 50 wt.-% $TiO_2$.

European patent application EP 2 223 905 A1 relates to a composition in the form of a solid-solid solution which is phase stable at 1150° C./36 hours and at 1200° C./4 hours, the composition comprising oxides of zirconium and cerium wherein the oxide of zirconium is enriched, an oxide of erbium, gadolinium, dysprosium, or yttrium as a stabilizer in an amount of 10% to 30% by weight, and optionally one or more dopants, a composition in the form of a solid-solid solution comprising oxides of zirconium and cerium wherein the oxide of zirconium is enriched, an oxide of erbium or oxide of dysprosium as a stabilizer in an amount of 10% to 30% by weight and optionally one or more dopant, the use of such compositions in a system for exhaust gas after treatment and a process which is appropriate for the preparation of such compositions.

Chinese patent application CN 16 26 437 A relates to a method for preparing a series of solid solutions of metal oxides through the carbamide combustion method. Urea is proportionally mixed with the nitrate of metals chosen from Ce—La, Ce—Zr, Ce—Ni, La—Al—Fe, La—Fe, and Mg (or Zn)—Co, and burned to obtain the solid solution of, among many others, $Ce_{(1-x)}Zr_xO_2$. $Ce_{0.9}Zr_{0.1}O_2$, $Ce_{0.5}Zr_{0.5}O_2$ and $Ce_{0.1}Zr_{0.9}O_2$ are specifically disclosed. Compounds with a very low value of x, such as 0.05, 0.045, 0.02 or even 0.01, are not disclosed.

SUMMARY

Taking into account the economic importance of carbamates as isocyanate precursors, it is highly desirable to provide further improvements regarding the catalyst-mediated preparation of carbamates. More specifically, carbamates should be prepared in high yield and with low amounts of by-products employing catalysts that can easily be separated off from the final product and re-used. The present invention addresses these needs.

In one aspect, the present invention is directed at a catalyst for preparing carbamates, in particular aromatic carbamates, comprising a binary oxide having the formula $L_{1-x}M_xO_2$, wherein L is a metal selected from the lanthanoid series and M is a metal selected from the group consisting of Sc, Y, Ti, Zr, Hf, metals from the lanthanoid series and metals from the actinoid series, and wherein x ranges from 0.01 to 0.05.

In another aspect, the present invention is directed at a method for preparing the catalyst of the invention, said method comprising the steps:
 I. Precipitating a catalyst precursor comprising the combination of aqueous solutions of salts of L and M in the presence of an oxidising agent;
 II. Separating off the catalyst precursor precipitated in step I;
 III. Calcining the catalyst precursor separated off in step II to yield the catalyst.

In yet another aspect, the present invention is directed at a method of producing a carbamate compound, comprising the step of reacting an organic amine, in particular an aromatic amine, with an organic dicarbonate, in particular a dialkyl carbonate, in the presence of the catalyst of the invention.

In yet another aspect, the present invention is directed at a process for producing an isocyanate, comprising producing a carbamate compound according to the inventive method and subjecting the carbamate to thermal or catalytic cleavage.

DETAILED DESCRIPTION

Within the context of the present invention, the term "lanthanoid series" is understood to encompass La, Ce, Pr, Nd, Pm, Sm, Eu, Gd, Tb, Dy, Ho, Er, Tm, Yb and Lu, as is well-known in the art. Likewise, the term "actinoid series" is understood to encompass Ac, Th, Pa, U, Np, Pu, Am, Cm, Bk, Cf, Es, Fm, Md, Ne and Lr. If both, "L" and "M", are taken from the lanthanoid series, different lanthanoid metals are chosen so as to arrive at a "binary oxide" as catalyst.

A brief summary of various possible embodiments of the invention firstly follows:

In a first embodiment of the inventive catalyst, which can be combined with all other embodiments, L is cerium.

In a second embodiment of the inventive catalyst, which can be combined with all other embodiments, M is selected from the group consisting of yttrium, zirconium, hafnium, lanthanum, praseodymium, samarium, europium and terbium, preferably from yttrium, zirconium, hafnium, samarium and europium.

In a third embodiment of the inventive catalyst, which is a particular variant of the second embodiment, M is zirconium.

In a fourth embodiment of the inventive catalyst, which can be combined with all other embodiments, x ranges from 0.02 to 0.05, or from 0.01 to 0.045, or from 0.02 to 0.045.

In a first embodiment of the inventive method for preparing the catalyst of the invention, which can be combined with all other embodiments, the oxidising agent is selected from the group consisting of hydrogen peroxide, nitric acid, perchloric acid, peroxydisulphuric acid, peroxymonosulphuric acid, chlorite, chlorate, perchlorate, hypochlorite, sodium perborate, and mixtures thereof, in particular hydrogen peroxide or mixtures of hydrogen peroxide and nitric acid.

In a second embodiment of the inventive method for preparing the catalyst of the invention, which can be combined with all other embodiments, the salts of L and M are independently of one another selected from the group consisting of nitrates, chlorides, sulphates and hydroxides, in particular nitrates and chlorides.

In a third embodiment of the inventive method for preparing the catalyst of the invention, which can be combined with all other embodiments, the precipitating in step I comprises adjusting the pH of the combined solutions of salts of L and M to a value of from 7.0 to 14.0, preferably to a value of from 9.0 to 11.0, in particular to 10.5.

In a fourth embodiment of the inventive method for preparing the catalyst of the invention, which is a particular variant of the third embodiment, the adjusting of the pH is affected by addition of a base, in particular an aqueous ammonia solution.

In a fifth embodiment of the inventive method for preparing the catalyst of the invention, which can be combined with all other embodiments, the separating off in step II is carried out by filtration or centrifugation.

In a sixth embodiment of the inventive method for preparing the catalyst of the invention, which can be combined with all other embodiments, the separating off in step II comprises washing of the catalyst precursor separated off.

In a seventh embodiment of the inventive method for preparing the catalyst of the invention, which can be combined with all other embodiments, the catalyst precursor separated off in step II is dried before being calcined in step III.

In an eighth embodiment of the inventive method for preparing the catalyst of the invention, which is a particular variant of the seventh embodiment, the drying is carried out in a static atmosphere, in particular in static air.

In a ninth embodiment of the inventive method for preparing the catalyst of the invention, which can be combined with all other embodiments, calcining the catalyst precursor in step III is carried out at a temperature of from 300° C. to 600° C., preferably at a temperature of from 450° C. to 550° C., in particular at a temperature of 500° C.

In a tenth embodiment of the inventive method for preparing the catalyst of the invention, which can be combined with all other embodiments, calcining the catalyst precursor in step III is carried out in a static atmosphere, in particular in static air.

In a first embodiment of the inventive method of producing a carbamate compound, which can be combined with all other embodiments, the organic dicarbonate is a dialkyl carbonate selected from the group consisting of dipropyl carbonate, diethyl carbonate, and dimethyl carbonate.

In a second embodiment of the inventive method of producing a carbamate compound, which can be combined with all other embodiments, the reaction is carried out at a molar ratio of organic dicarbonate to organic amine of from 10:1 to 50:1, preferably of from 25:1 to 35:1, particularly preferably 30:1.

In a third embodiment of the inventive method of producing a carbamate compound, which can be combined with all other embodiments, the reaction of the organic amine with the dialkyl carbonate is carried out at a catalyst loading ranging of from 5 $m^2$/mmol amine to 40 $m^2$/mmol amine, preferably of from 15 $m^2$/mmol amine to 25 $m^2$/mmol amine, particularly preferably 20 $m^2$/mmol amine, where "$m^2$" refers to the BET surface area of the catalyst.

In a fourth embodiment of the inventive method of producing a carbamate compound, which can be combined with all other embodiments, the reaction of the organic amine with the organic dicarbonate is carried out at a temperature ranging from 100° C. to 190° C. for a reaction time ranging from 2 h to 24 h, preferably at a temperature ranging from 120° C. to 160° C. for a reaction time ranging from 3 h to 10 h, more preferably at a temperature ranging from 130° C. to 150° C. and a reaction time from 6 h to 8 h, particularly preferably at a temperature of 140° C. and a reaction time of 7 h.

In a fifth embodiment of the inventive method of producing a carbamate compound, which can be combined with all other embodiments, the reaction is carried out under autogenous pressure.

In a sixth embodiment of the inventive method of producing a carbamate compound, which can be combined with all other embodiments, wherein the organic amine comprises aniline, 2,4-diamino-N-phenylaniline, o-, m-, and p-phenylenediamine, 2,4-diaminotoluene, 2,6-diaminotoluene, 1,2,4,5-tetraaminobenzene, 4-methoxy-m-phenylenediamine, 4-amino-N-phenylaniline, 2-amino-N-methylaniline, N-isobutyl-p-phenyldiamine, o-, m-, and p-xylylenediamine, N-isoamyl-p-phenylenediamine, N-benzyl-p-phenylenediamine, N-cyclohexyl-p-diphenylenediamine, N,N'-di(n-propyl)-p-phenylenediamine, N-(n-butyl)-N'-benzyl-p-phenylenediamine, N,N'-dibenzyl-p-phenylenediamine, N-ethyl-m-phenylenediamine, N-ethyl-o-phenylenediamine, N-methyl-m-phenylenediamine, N,N'-diethyl-p-phenylenediamine, N-methyl-N-(n-propyl)-p-phenylenediamine, 4,4'-oxydianiline, 4,4'ethylenedianiline, 2,4-bis(4-aminobenzyl)aniline, 4,4'-methylenebis(N,N-dimethylaniline), 4,4'methylenebis(N-methylaniline), benzidine; N,N,N',N'-tetramethylbenzidine, bis(3,4-diaminophenyl)methane, bis(3-methyl-4-aminophenyl)methane, 2,2'-methylenedianiline, 2,4'-methylene dianiline, 4,4'-methylene dianiline, 1,6-hexamethylene diamine, isophorone diamine, (2-aminocyclohexyl)-(4'-aminocyclohexyl)-methane, bis-(4-aminocyclohexyl)-methane or a mixture of two or more of the aforementioned organic amines, whereby in case the organic amine comprises methylene dianiline, higher oligomers of methylene dianiline having three or more six-membered aromatic rings are optionally also contained in the organic amine.

In a seventh embodiment of the inventive method of producing a carbamate compound, which is a particular variant of the sixth embodiment, the organic amine comprises aniline, 2,4-diaminotoluene, 2,6-diaminotoluene, 2,2'-methylene dianiline, 2,4'-methylene dianiline, 4,4'-methylene dianiline or a mixture of two or more of the aforementioned organic amines, whereby in case the organic amine comprises methylene dianiline, higher oligomers of methylene dianiline having three or more six-membered aromatic rings are optionally also contained in the organic amine.

In an eighth embodiment of the inventive method of producing a carbamate compound, which is a particular variant of the seventh embodiment, the organic amine comprises (i) 2,4-diaminotoluene and 2,6-diaminotoluene or comprises (ii) 2,4'-methylene dianiline and 4,4'-methylene dianiline or comprises (iii) 2,2'-methylene dianiline, 2,4'-methylene dianiline and 4,4'-methylene dianiline, whereby in cases (ii) and (iii), higher oligomers of methylene dianiline having three or more six-membered aromatic rings are optionally also contained in the organic amine.

The invention will now be described in greater detail referring inter alia to the different embodiments described in short above. It is to be understood that different embodiments may be combined with each in any conceivable manner unless the technical context suggests otherwise.

The catalyst of the present invention is a binary oxide having the formula $L_{1-x}M_xO_2$, wherein L is a metal selected from the lanthanoid series and M is a metal selected from the group consisting of Sc, Y, Ti, Zr, Hf, metals from the lanthanoid series (other than L) and metals from the actinoid series, and wherein x ranges from 0.01 to 0.05. Since the molar ratio of M:L is defined as x/[1−x] in this formula, and x+[1−x]=1, x can be referred to as the molar fraction of M in the total amount of L and M, i.e. $x=n_M/[n_L+n_M]$ (n=molar amount). If, for example, x=0.05, 5 mole percent of all metals (i.e. M and L) are M metals.

Preferably, L is Ce, and M is preferably yttrium, zirconium, hafnium, lanthanum, praseodymium, samarium, europium or terbium, more preferably yttrium, zirconium, hafnium, samarium or europium. Most preferred, L is Ce and M is zirconium.

The values for x range preferably of from 0.02 to 0.05, more preferably from 0.02 to 0.045.

The average crystallite size of the final catalyst is preferably of from 3 nm to 14 nm, more preferably of from 8 nm to 10 nm. Within the context of the present invention, particle sizes are determined from XRD analysis by applying the Scherrer equation to the most prominent reflection as described in *J. Appl. Cryst.* 11 (1978), 102-113.

The BET surface area is preferably higher than 60 $m^2 g^{-1}$, as determined by the BET method. Within the context of the present invention, for the purpose of applying the BET method, nitrogen isotherms at 77 K are measured on a Quantachrome Quadrasorb SI analyzer. Prior to the analysis, the samples are outgassed to 50 mbar at 300° C. for 3 h. The BET method is applied to calculate the specific surface area by using the calculations originally described by Brunauer, Emmett and Teller in *J. Am. Chem. Soc.* 1938, 60, 309.

The method for preparing the catalyst of the invention comprises the following steps:
  I. Precipitating a catalyst precursor comprising combining aqueous solutions of salts of L and M in the presence of an oxidising agent;
  II. Separating off the catalyst precursor precipitated in step I;
  III. Calcining the catalyst precursor separated off in step II to yield the catalyst.

In step I of the method for preparing the catalyst, a catalyst precursor is precipitated by combining aqueous solutions of salts of L and M under appropriate conditions. In this step, the two metals L and M co-precipitate out their respective aqueous precursor salt solutions. Suitable salt solutions comprise nitrates, chlorides, sulphates, hydroxides, and, in particular nitrates or chlorides. Depending on the nature of L and M, these metals may be present in their salts as oxygen-containing cations, such as $UO_2^{2+}$, as the skilled person knows.

Appropriate conditions comprise using an oxidising agent, preferably, hydrogen peroxide, nitric acid, perchloric acid, peroxydisulphuric acid, peroxymonosulphuric acid, chlorite, chlorate, perchlorate, hypochlorite, sodium perborate, and mixtures thereof, and, in particular hydrogen peroxide ($H_2O_2$) or hydrogen peroxide together with the amount of nitric acid used for dissolving the metal precursor. Without wishing to be bound by any theory, it is believed that the oxidising agent transforms the precursor metal species (in particular $Ce^{3+}$) into a more easily hydrolysable form (in particular $Ce^{4+}$). Hydrogen peroxide is believed to have the additional advantage of forming hydroperoxide complexes, which are believed to disrupt the formation of compact "L-O-L" (or "M-O-M") networks during the crystallisation process, thus favouring the production of highly-dispersed nanocrystallites of cerium oxide (see, Pappacena et al., *Int. J. Hydrogen Energy* 2012, 37, 1698-1709; *Stud. Surf. Sci. Catal.* 2010, 175, 835-838). The catalyst precursor thus prepared contains hydroxide groups.

Preferably, the pH of the combined aqueous solutions of salts of L and M is then adjusted to a value of from 7.0 to 14.0, preferably to a value of from 9.0 to 11.0, in particular to 10.5. To this end, it is preferred to add aqueous ammonia solution until the desired pH is reached. Alternatively, urea may also be used to adjust the pH. Other bases such as metal hydroxides and basic salts, e.g., sodium hydroxide, sodium carbonate, calcium hydroxide, and potassium hydroxide, are, however, also possible. Within the context of the present invention, pH values refer to values measured at 25° C.

After combining the aqueous salt solutions of L and M, adding the oxidising agent and, preferably, adjusting the pH to a value in the above specified ranges by the addition of a base such as those mentioned above, L and M species co-precipitate in the form of a catalyst precursor. The slurry thus obtained may be stirred or otherwise agitated for some time, preferably of from 0.5 hours to 24 hours, more preferably from 1 hour to 12 hours, even more preferred of from 2 hours to 6 hours and in particular for 4 hours.

The entire step I is preferably carried out at ambient temperature. The addition of reagents is preferably carried out at a rate so as to avoid significant heating of the reaction mixture due to exothermic reactions. Thus, the pH measured at the temperature at which step I is performed will generally not, or only to an insignificant extent, deviate from the pH value for 25° C.

In step II, the catalyst precursor that has precipitated in step I is separated off, preferably by filtration or centrifugation of the slurry obtained in step I. The solid catalyst precursor thus isolated is preferably purified by washing, in particular by washing with deionised water, ethanol or a mixture of both, in particular until the filtrate reaches pH 7.0.

Before being subjected to calcination in step III, it is preferable to remove excessive water by drying at elevated temperature, preferably at a temperature of from 50° C. to 200° C., more preferably at a temperature of from 60° C. to 150° C., even more preferred at a temperature of from 80° C. to 125° C., and in particular at 100° C., for 1 hour to 48 hours, preferably for 2 hours to 24 hours, even more preferred for 6 hours to 18 hours, and in particular for 12 hours. The drying is preferably carried out in a static atmosphere, i.e. not in vacuum, in particular in static air. An inert atmosphere such as nitrogen or a noble gas (e.g. He, Ne, Ar) may, however, also be used.

The thus obtained catalyst precursor is calcined in step III. In this calcination step, the temperature should be sufficient to result in the transformation of the hydroxide into oxide groups. The calcination temperature is preferably of from 300° C. to 600° C., more preferably of from 450° C. to 550° C., in particular 500° C. Preferably, the catalyst precursor is heated to the selected temperature within the above ranges at a rate of from 1° C. min$^{-1}$ to 15° C. min$^{-1}$, more preferably of from 2° C. min$^{-1}$ to 10° C. min$^{-1}$, even more preferred of from 3° C. min$^{-1}$ to 8° C. min$^{-1}$, and in particular at 5° C. min$^{-1}$. Calcination is preferably conducted for 0.5 hours to 15 hours, more preferably for 1 hour to 10 hours, even more preferred for 2 hours to 8 hours, and in particular for 5 hours.

Calcination is preferably carried out in a static atmosphere, preferably in air or an inert atmosphere such as nitrogen or noble gas atmosphere, in particular in static air. It is, however, also possible to carry out calcination in vacuum or under the influence of the flow of a gas such as air, nitrogen or a noble gas, i.e. under "dynamic conditions".

An exemplary embodiment of steps I-III is described in the following: The L and M precursors are each dissolved in deionized water in such a way that the overall weight ratio [L+M]:H$_2$O is 1:10 and using the corresponding amount of M precursor to reach the desired x molar fraction at ambient temperature, followed by the addition of H$_2$O$_2$ or H$_2$O$_2$ with the amounts of nitric acid used for dissolving the metal precursor at ambient temperature to obtain a molar H$_2$O$_2$: (L+M) ratio of 3:1. The precipitation is obtained by adding aqueous ammonia solution at ambient temperature until a pH of 10.5 is reached. The slurry is stirred for 4 hours at room temperature (step I). The precipitate is then separated from the solution by filtration, washed with deionized water and dried at 100° C. in static air for 12 hours (step II). Finally, the thus obtained catalyst precursor is calcined in static air at 500° C. for 5 hours (step III).

The inventive method of producing a carbamate compound comprises the step of reacting an organic amine, in particular an aromatic amine, with an organic dicarbonate, in particular a dialkyl carbonate, in the presence of the catalyst of the invention. Preferably, dialkyl carbonates are used in this step. Dipropyl carbonate, diethyl carbonate and dimethyl carbonate, in particular dimethyl carbonate are preferred.

In any case the molar ratio of organic dicarbonate to organic amine is preferably of from 10:1 to 50:1, more preferably of from 25:1 to 35:1, and is in particular 30:1.

The inventive catalyst is preferably used in the method for producing carbamates at a catalyst loading ranging of from 5 m$^2$/mmol amine to 40 m$^2$/mmol amine, preferably of from 15 m$^2$/mmol amine to 25 m$^2$/mmol amine, and in particular of 20 m$^2$/mmol amine, where "m$^2$" refers to the BET surface area of the catalyst. These values are particularly suitable if the organic amine is a diamine, i.e. carries two amino groups.

As regards process conditions, the inventive method for producing carbamates may be carried out under comparatively mild conditions such as at a temperature ranging from 100° C. to 190° C. for a reaction time ranging from 2 h to 24 h, preferably at a temperature ranging from 120° C. to 160° C. for a reaction time ranging from 3 h to 10 h, more preferably at a temperature ranging from 130° C. to 150° C. and a reaction time from 6 h to 8 h, and in particular at a temperature of 140° C. and a reaction time of 7 h. The reaction time refers to the time the reaction is allowed to proceed once the desired temperature has been reached.

The inventive method for producing carbamates is preferably carried out under autogenous pressure, i.e. the reagents are introduced into a pressure-resistant apparatus (such as an autoclave), which is then closed, the pressure being the pressure that develops as a result of the chemical reaction taking place. The pressure-resistant apparatus may be charged with an inert atmosphere such as nitrogen or a noble gas (e.g. He, Ne, Ar) before starting the chemical reaction.

If the inventive method is to be carried out continuously, which is preferred on an industrial scale, a continuous flow reactor can be used. Under continuous conditions, the reactants will pass through a fixed catalyst bed. The flow of the reactants is controlled by a back pressure regulator located after the reactor, which ultimately determines the residence time, and therefore the conversion of the reactants.

Any organic amine, aliphatic, araliphatic or aromatic, may be used in the context of the present invention. The organic amine may have one or more, in particular two, secondary or primary amino groups, primary amino groups being preferred. The only limitation may arise from the possible further applications the carbamate produced is supposed to be subjected to. Within the context of the present invention, the most preferred application is the cleavage of the carbamate to give an isocyanate, setting free an alcohol in the process. For this purpose, only primary amino groups are suitable, and the organic amine should be devoid of any other substituents that might undergo undesired reactions with isocyanate groups.

The organic amine to be used in the inventive method for producing carbamates preferably is aniline, 2,4-diamino-N-phenylaniline, o-, m-, and p-phenylenediamine, 2,4-diaminotoluene, 2,6-diaminotoluene, 1,2,4,5-tetraaminobenzene, 4-methoxy-m-phenylenediamine, 4-amino-N-phenylaniline, 2-amino-N-methylaniline, N-isobutyl-p-phenyldiamine, o-, m-, and p-xylylenediamine, N-isoamyl-p-phenylenediamine, N-benzyl-p-phenylenediamine, N-cyclohexyl-p-diphenylenediamine, N,N'-di(n-propyl)-p-phenylenediamine, N-(n-butyl)-N'-benzyl-p-phenylenediamine, N,N'-dibenzyl-p-phenylenediamine, N-ethyl-m-phenylenediamine, N-ethyl-o-phenylenediamine, N-methyl-m-phenylenediamine, N,N'-diethyl-p-phenylenediamine, N-methyl-N-(n-propyl)-p-phenylenediamine, 4,4'-oxydianiline, 4,4'ethylenedianiline, 2,4-bis(4-aminobenzyl)aniline, 4,4'-methylenebis(N,N-dimethylaniline), 4,4'methylenebis(N-methylaniline), benzidine; N,N,N',N'-tetramethylbenzidine, bis(3,4-diaminophenyl)methane, bis(3-methyl-4-aminophenyl)methane, methylene dianiline ("MDA"), in particular the isomers 2,2'-methylene dianiline ("2,2'-MDA"), 2,4'-methylene dianiline ("2,4'-MDA") and/or 4,4'-methylene dianiline ("4,4'-MDA"), whereby the MDA may optionally also comprise higher oligomers having three or more six-membered aromatic rings (known as "polymeric MDA"), 1,6-hexamethylene diamine, isophorone diamine, (2-aminocylohexyl)-(4'-aminocylohexyl)-methane, bis-(4-aminocyclohexyl)-methane or a mixture of two or more of the aforementioned organic amines.

Even more preferred, the organic amine is aniline, 2,4-diaminotoluene, 2,6-diaminotoluene, 2,2'-methylene dianiline, 2,4'-methylene dianiline, 4,4'-methylene dianiline, whereby any MDA isomer may optionally also comprise higher oligomers having three or more six-membered aromatic rings, or a mixture of two or more of the aforementioned organic amines.

Most preferred, the organic amine is (i) a mixture of 2,4-diaminotoluene and 2,6-diaminotoluene or is (ii) a mixture of 2,4'-methylene dianiline and 4,4'-methylene dianiline or is (iii) a mixture of 2,2'-methylene dianiline, 2,4'-methylene dianiline, and 4,4'-methylene dianiline, whereby in cases (ii) and (iii) the methylene dianiline may optionally comprise higher oligomers of methylene dianiline having three or more six-membered aromatic rings.

In contrast to homogeneous catalysts, the inventive method for producing carbamates allows for an easy recovery of the catalyst from the reaction mixture. The recovered catalyst can be re-used in subsequent reaction cycles (see Example 15).

As already mentioned, in yet another aspect the invention is directed to a process for producing an isocyanate by cleavage of the carbamate produced with the inventive method. The reaction is well-known in the art and can be induced thermally or catalytically. All processes known in the prior art can be used.

EXAMPLES

General Remarks

The catalytic results presented below are based on a series of experiments employing the different heterogeneous catalysts that have been prepared according to Examples 1 to 7. Catalytic assays were at least duplicated (a minimum of two reactions per catalyst were performed). Furthermore, two samples for HPLC quantitative analysis were made up for each reaction mixture and were quantified by HPLC analysis using calibration curves of external standards.

As test substrates for carbamate production, 2,4-TDA and dimethyl carbonate were used, as shown in the following scheme:

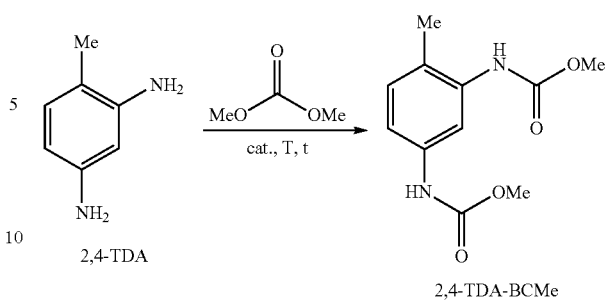

Reactions were performed in an autoclave under nitrogen atmosphere. The reaction time of 7 hours refers to the time the reaction is allowed to proceed after the desired temperature has been reached. Heating-up the autoclave takes 30 min for reactions at 140° C.

Dimethyl carbonate (99%) was purchased from Aldrich and was dried with 4 Å molecular sieves. Water content analysis of the organic carbonates (Karl Fischer method) was performed; water concentration was always below 30 ppm. 2,4-TDA (98%) was purchased from Aldrich used without further purification.

Crude product mixtures derived from the methoxycarbonylation reaction of 2,4-TDA were analysed by quantitative HPLC analysis using calibration curves of external standards. The analytical conditions were as follows:

Kromasil 100 C18 5 µm 4.6×150 mm, RT, 1.0 mL/min, Injection=5 µL, UV detection 225 nm, Eluent A:100 mL $CH_3CN$, 900 mL $H_2O$, 0.01M $NH_4Ac$. Eluent B: 900 mL $CH_3CN$, 100 mL $H_2O$, 0.01M $NH_4Ac$. Gradient: 0 min 100% A, 22 min 100% A; 48 min 80% A, 20% B; 60 min 55% A, 45% B; 80 min Stop. Retention times: Rt(2,4-TDA)=7.5 min, Rt(2,4-TDA-M-oMe)=15.0 min, Rt(2,4-TDA-M-pMe)=20.0 min, Rt(2,4-TDA-MC-oMe)=22.4 min, Rt(2,4-TDA-MC-pMe)=30.8 min, Rt(2,4-TDA-BMe)=42.0 min. Rt(2,4-TDA-BCMe)=45.1 min.

Preparation of the Catalyst

Example 1 (According to the Invention)

The binary oxide $Ce_{0.98}Zr_{0.02}O_2$ with a zirconium molar fraction of 2% was prepared by co-precipitation in the presence of $H_2O_2$. $Ce(NO_3)_3 \cdot 6H_2O$ (Acros, 99.5%) and the corresponding amount of zirconyl nitrate solution (Aldrich, 35% in dilute nitric acid) were dissolved in deionized water (in a weight ratio of (Ce precursor+Zr precursor)=1:10) under stirring at room temperature, $H_2O_2$ was poured into the solution to obtain a molar $H_2O_2$:(Ce+Zr) ratio of 3. The precipitation was obtained by adding aqueous ammonia solution until a pH of 10.5 was reached. The slurry was stirred for 4 hours at room temperature, and the precipitate formed was separated by filtration, washed with deionized water until neutral pH, dried at 100° C. in static air for 12 hours, and calcined at 500° C. (5° C. $min^{-1}$) in static air for 5 h. Phase composition was confirmed by XRD (X-Ray diffraction), crystallite size was 9 nm calculated from the Scherrer equation, and BET surface area was 69 $m^2 g^{-1}$. The resulting catalyst was named catalyst A.

Example 2 (According to the Invention)

Following the procedure of Example 1, the binary oxide $Ce_{0.95}Zr_{0.05}O_2$ with a zirconium molar fraction of 5% was prepared. Phase composition was confirmed by XRD (X-Ray diffraction), crystallite size was 9 nm calculated from the Scherrer equation, and BET surface area was 79 m$^2$ g$^{-1}$. The resulting catalyst was named catalyst B.

Example 3 (According to the Invention)

Following the procedure of Example 1, the binary oxide Ce$_{0.95}$Eu$_{0.05}$O$_2$ with an europium molar fraction of 5% was prepared, employing Eu(NO$_3$)$_3$.6H$_2$O (ABCR-Chemicals, 99.9%) as precursor. Phase composition was confirmed by XRD (X-Ray diffraction), crystallite size was 8 nm calculated from the Scherrer equation, and BET surface area was 73 m$^2$ g$^{-1}$. The resulting catalyst was named catalyst C.

Example 4 (According to the Invention)

Following the procedure of Example 1, the binary oxide Ce$_{0.98}$Y$_{0.02}$O$_2$ with an yttrium molar fraction of 2% was prepared, employing Y(NO$_3$)$_3$.6H$_2$O (ABCR-Chemicals, 99.9%) as precursor. Phase composition was confirmed by XRD, crystallite size was 9 nm calculated from the Scherrer equation, and BET surface area was 71 m$^2$ g$^{-1}$. The resulting catalyst was named catalyst D.

Example 5 (According to the Invention)

Following the procedure of Example 1, the binary oxide Ce$_{0.98}$Sm$_{0.02}$O$_2$ oxide with a samarium molar fraction of 2% was prepared, employing Sm(NO$_3$)$_3$.6H$_2$O (Acros Organics, 99.9%) as precursor. Phase composition was confirmed by XRD, crystallite size was 10 nm calculated from the Scherrer equation, and BET surface area was 73 m$^2$ g$^{-1}$. The resulting catalyst was named catalyst E.

Example 6 (According to the Invention)

Following the procedure of Example 1, the binary oxide Ce$_{0.98}$Hf$_{0.02}$O$_2$ with a hafnium molar fraction of 2% was prepared, employing HfCl$_4$ (Strem Chemicals, 99.9%) as precursor. Phase composition was confirmed by XRD, crystallite size was 9 nm calculated from the Scherrer equation, and BET surface area was 84 m$^2$ g$^{-1}$. The resulting catalyst was named catalyst F.

Example 7 (Comparative Example)

CeO$_2$ was precipitated from a Ce(NO$_3$)$_3$.6H$_2$O (Acros, 99.5) solution following the procedure of Example 1 with the exception that no M dopant was used. Phase composition was confirmed by XRD, crystallite size was 12 nm calculated from the Scherrer equation, and BET surface area was 64 m$^2$ g$^{-1}$. The resulting catalyst was named catalyst G.

Preparation of Aromatic Carbamates

Example 8 (According to the Invention)

0.40 g 2,4-toluenediamine, 8.8 g dimethyl carbonate, and 0.84 g of catalyst A were placed with a magnetic stirrer in a PTFE vessel in a 25 mL autoclave. The reaction was performed after reaching an internal temperature of 140° C. and maintained at this temperature for 7 hours under autogenous pressure. After the completion of the reaction, the autoclave was cooled down and the reaction mixture analysed by HPLC.

Biscarbamate yield: 88%. Combined yield of mono- and biscarbamates: 95%.

Example 9 (According to the Invention)

0.40 g 2,4-toluenediamine, 8.8 g dimethyl carbonate, and 0.82 g of catalyst B were placed with a magnetic stirrer in a PTFE vessel in a 25 mL autoclave, otherwise following the reaction procedure of Example 8.

Biscarbamate yield: 82%. Combined yield of mono- and biscarbamates: 93%.

Example 10 (According to the Invention)

0.40 g 2,4-toluenediamine, 8.8 g dimethyl carbonate, and 0.89 g of catalyst C were placed with a magnetic stirrer in a PTFE vessel in a 25 mL autoclave, otherwise following the reaction procedure of Example 8.

Biscarbamate yield: 82%. Combined yield of mono- and biscarbamates: 93%.

Example 11 (According to the Invention)

0.40 g 2,4-toluenediamine, 8.8 g dimethyl carbonate, and 0.89 g of catalyst D were placed with a magnetic stirrer in a PTFE vessel in a 25 mL autoclave, otherwise following the reaction procedure of Example 8.

Biscarbamate yield: 84%. Combined yield of mono- and biscarbamates: 93%.

Example 12 (According to the Invention)

0.40 g 2,4-toluenediamine, 8.8 g dimethyl carbonate, and 0.89 g of catalyst E were placed with a magnetic stirrer in a PTFE vessel in a 25 mL autoclave, otherwise following the reaction procedure of Example 8.

Biscarbamate yield: 83%. Combined yield of mono- and biscarbamates: 93%.

Example 13 (According to the Invention)

0.40 g 2,4-toluenediamine, 8.8 g dimethyl carbonate, and 0.77 g of catalyst F were placed with a magnetic stirrer in a PTFE vessel in a 25 mL autoclave, otherwise following the reaction procedure of Example 8.

Biscarbamate yield: 81%. Combined yield of mono- and biscarbamates: 93%.

Example 14 (Comparative Example)

0.40 g 2,4-toluenediamine, 8.8 g dimethyl carbonate, and 1.01 g of catalyst G were placed with a magnetic stirrer in a PTFE vessel in a 25 mL autoclave, otherwise following the reaction procedure of Example 8.

Biscarbamate yield: 83%. Combined yield of mono- and biscarbamates: 90%.

Table 1 summarizes the results of examples 8-14.

TABLE 1

Methoxycarbonylation reactions of 2,4-TDA using catalysts A □ G.[a]

| Ex. | Catalyst | | Conversion (%) | Combined Yield (%) [b] | BCMe Yield (%) [c] | Alk. Carb. (Σ area %) [d] |
|---|---|---|---|---|---|---|
| 14 | CeO$_2$[e] | G | >99 | 90 | 83 | 3 |
| 8 | Ce$_{0.98}$Zr$_{0.02}$O$_2$ | A | >99 | 95 | 88 | 3 |
| 9 | Ce$_{0.95}$Zr$_{0.05}$O$_2$ | B | >99 | 93 | 82 | 3 |
| 10 | Ce$_{0.95}$Eu$_{0.05}$O$_2$ | C | >99 | 93 | 82 | 3 |
| 11 | Ce$_{0.98}$Y$_{0.02}$O$_2$ | D | >99 | 93 | 84 | 3 |

TABLE 1-continued

Methoxycarbonylation reactions of 2,4-TDA using catalysts A – G.[a]

| Ex. | Catalyst | Code | Conversion (%) | Combined Yield (%) [b] | BCMe Yield (%) [c] | Alk. Carb. (Σ area %) [d] |
|---|---|---|---|---|---|---|
| 12 | $Ce_{0.98}Sm_{0.02}O_2$ | E | >99 | 93 | 83 | 3 |
| 13 | $Ce_{0.98}Hf_{0.02}O_2$ | F | >99 | 93 | 81 | 4 |

[a]Values expressed as an average of all independent runs. Catalyst loading was adjusted to reach a catalyst surface area of 20 m²/mmol 2,4-TDA. (The catalysts were dosed based on their surface area. The specific surface area of each catalyst was measured prior to the catalytic reaction and then the catalyst was dosed based on a fixed and predetermined ratio of surface area per mmol of the substrate which was 20 m²/mmol 2,4-TDA in these experiments.)
[b]Combined yield stand for the sum of the yield of the target biscarbamate and its precursors (i.e. the two corresponding monocarbamates).
[c]Yield of biscarbamate.
[d]Sum of the percentage of peak areas of all alkylated carbamates.
[e]Catalyst prepared following the procedure of examples 1-6 in the absence of metal M.

As can be seen from Table 1, the combined yields of mono and biscarbamates are significantly higher in case of the inventive catalysts as compared to $CeO_2$.

Example 15 (According to the Invention)

Five consecutive catalytic tests were conducted with the catalyst A and the catalyst G under the conditions described in Example 8. After each run, the used catalyst was recovered by filtration, washed with acetone (5×5 mL), and dried at 120° C. in static air for 2 hours. Prior to the next catalytic test, the BET surface area was determined and the required amount of catalyst was calculated to be constant at 20 m²/mmol 2,4-TDA in all the experiments.

Table 2 summarizes the results.

TABLE 2

Results of the consecutive methoxycarbonylation reactions of 2,4-TDA using catalysts A and G.[a]

| Catalyst | Code | Cycle | Conversion (%) | Combined Yield (%)[b] | BCMe Yield (%)[c] | Alk. Carb. (Σ area %)[d] |
|---|---|---|---|---|---|---|
| $CeO_2$[e] | G | #1 | >99 | 90 | 83 | 3 |
|  |  | #2 | >99 | 92 | 83 | 3 |
|  |  | #3 | >99 | 86 | 60 | 4 |
|  |  | #4 | 99 | 66 | 43 | 7 |
|  |  | #5 | 89 | 42 | 8 | 15 |
| $Ce_{0.98}Zr_{0.02}O_2$ | A | #1 | >99 | 96 | 88 | 3 |
|  |  | #2 | >99 | 90 | 76 | 4 |
|  |  | #3 | >99 | 92 | 79 | 4 |
|  |  | #4 | 99 | 80 | 40 | 7 |
|  |  | #5 | 98 | 54 | 22 | 12 |

[a]Values expressed as an average of all independent runs. Catalyst loading was adjusted to reach a catalyst surface area of 20 m²/mmol 2,4-TDA. (The catalysts were dosed based on their surface area. The specific surface area of each catalyst was measured prior to the catalytic reaction and then the catalyst was dosed based on a fixed and predetermined ratio of surface area per mmol of the substrate which was 20 m²/mmol 2,4-TDA in these experiments.)
[b]Combined yield stand for the sum of the yield of the target biscarbamate and its precursors (i.e. the two corresponding monocarbamates).
[c]Yield of biscarbamate.
[d]Sum of the percentage of peak areas of all alkylated carbamates.
[e]Catalyst prepared following the procedure of examples 1-6 in the absence of metal M.

The invention claimed is:

1. A catalyst for preparing carbamates, comprising a binary oxide having the formula $L_{1-x}M_xO_2$, wherein L is a metal selected from the lanthanoid series and M is a metal selected from the group consisting of scandium, yttrium, titanium, zirconium, hafnium, a metal from the lanthanoid series and a metal from the actinoid series, and wherein x ranges from 0.01 to 0.05.

2. The catalyst of claim 1, wherein L is cerium.

3. The catalyst of claim 1, wherein M is selected from the group consisting of yttrium, zirconium, hafnium, lanthanum, praseodymium, samarium, europium and terbium.

4. The catalyst of claim 3, wherein M is zirconium.

5. The catalyst of claim 1, wherein x ranges from 0.01 to 0.045.

6. A method for preparing the catalyst of claim 1, comprising:
  I. precipitating a catalyst precursor by combining an aqueous solution of a salt of the metal L and an aqueous solution of a salt of the metal M in the presence of an oxidizing agent;
  II. separating off the catalyst precursor precipitated in step I; and
  III. calcining the catalyst precursor separated off in step II to yield the catalyst.

7. The method of claim 6, wherein the oxidizing agent is selected from the group consisting of hydrogen peroxide, nitric acid, perchloric acid, peroxydisulphuric acid, peroxymonosulphuric acid, chlorite, chlorate, perchlorate, hypochlorite, sodium perborate, and mixtures thereof.

8. The method of claim 6, wherein the salt of the metal L and the salt of the metal M are independently of one another selected from the group consisting of nitrates, chlorides, sulphates and hydroxides.

9. The method of claim 6, wherein the precipitating in step I comprises adjusting the pH of the combined solutions of the salt of the metal L and the salt of the metal M to a value of from 7.0 to 14.0.

10. The method of claim 9, wherein the adjusting of the pH is affected by addition of a base.

11. A method of producing a carbamate compound, comprising reacting an organic amine with an organic dicarbonate in the presence of the catalyst of claim 1.

12. The method of claim 11, wherein the organic dicarbonate comprises one or more of dipropyl carbonate, diethyl carbonate, and dimethyl carbonate.

13. The method of claim 11, wherein the reaction is carried out at a molar ratio of organic dicarbonate to organic amine of from 10:1 to 50:1.

14. The method of claim 11, wherein the reaction is carried out under autogenous pressure.

15. The method of claim 11, wherein the organic amine comprises aniline, 2,4-diamino-N-phenylaniline, o-, m-, or p-phenylenediamine, 2,4-diaminotoluene, 2,6-diaminotoluene, 1,2,4,5-tetraaminobenzene, 4-methoxy-m-phenylenediamine, 4-amino-N-phenylaniline, 2-amino-N-methylaniline, N-isobutyl-p-phenyldiamine, o-, m-, or p-xylylenediamine, N-isoamyl-p-phenylenediamine, N-benzyl-p-phenylenediamine, N-cyclohexyl-p-diphenylenediamine, N,N'-di(n-propyl)-p-phenylenediamine, N-(n-butyl)-N'-benzyl-p-phenylenediamine, N,N'-dibenzyl-p-phenylenediamine, N-ethyl-m-phenylenediamine, N-ethyl-o-phenylenediamine, N-methyl-m-phenylenediamine, N,N'-diethyl-p-phenylenediamine, N-methyl-N-(n-propyl)-p-phenylenediamine, 4,4'-oxydianiline, 4,4'ethylenedianiline, 2,4-bis(4-aminobenzyl)aniline, 4,4'-methylenebis(N,N-dimethylaniline), 4,4'methylenebis(N-methylaniline), benzidine; N,N,N',N'-tetramethylbenzidine, bis(3,4-diaminophenyl)methane, bis(3-methyl-4-aminophenyl)methane, 2,2'-methylene dianiline, 2,4'-methylene dianiline, 4,4'-methylene dianiline, 1,6-hexamethylene diamine, isophorone diamine, (2-aminocylohexyl)-(4'-aminocylohexyl)-methane, bis-(4-aminocyclohexyl)-methane or a mixture of two or more of the aforementioned organic amines, whereby in case the organic amine comprises methylene dianiline, higher oligomers of methylene dianiline having three or more six-membered aromatic rings are optionally also contained in the organic amine.

16. A process for producing an isocyanate, comprising producing a carbamate compound according to the method of claim 11 and subjecting the carbamate to thermal or catalytic cleavage.

* * * * *